United States Patent
Akella et al.

(10) Patent No.: US 7,341,999 B2
(45) Date of Patent: *Mar. 11, 2008

(54) POVIDONE-CONTAINING CARRIERS FOR POLYPEPTIDE GROWTH FACTORS

(75) Inventors: Rama Akella, Austin, TX (US); John Ranieri, Atlanta, GA (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/338,914

(22) Filed: Jan. 25, 2006

(65) Prior Publication Data

US 2006/0128625 A1      Jun. 15, 2006

Related U.S. Application Data

(60) Division of application No. 10/027,669, filed on Dec. 21, 2001, now Pat. No. 6,992,066, which is a continuation-in-part of application No. 09/748,038, filed on Dec. 22, 2000, now Pat. No. 7,087,577, which is a continuation-in-part of application No. 09/173,989, filed on Oct. 16, 1998, now Pat. No. 6,211,157.

(51) Int. Cl.
  *A61K 38/18* (2006.01)
  *A61K 47/30* (2006.01)

(52) U.S. Cl. .............. 514/21; 424/486; 424/549; 514/8; 514/12; 514/772.5

(58) Field of Classification Search .............. None
See application file for complete search history.

(56) References Cited

U.S. PATENT DOCUMENTS

| | | | |
|---|---|---|---|
| 3,927,205 A | 12/1975 | Ohno et al. | 424/80 |
| 4,699,788 A | 10/1987 | Catsimpoolas et al. | 424/104 |
| 4,895,838 A | 1/1990 | McCluer et al. | 514/54 |
| 4,900,673 A | 2/1990 | Harper et al. | 435/199 |
| 4,950,483 A | 8/1990 | Ksander et al. | 424/422 |
| 5,116,738 A | 5/1992 | Wang et al. | 435/69.1 |
| 5,141,905 A | 8/1992 | Rosen et al. | 435/69.1 |
| 5,187,076 A | 2/1993 | Wozney et al. | 435/69.1 |
| 5,219,576 A | 6/1993 | Chu et al. | 424/484 |
| 5,290,763 A | 3/1994 | Poser et al. | 514/21 |
| 5,318,957 A | 6/1994 | Cid et al. | 514/8 |
| 5,328,695 A | 7/1994 | Lucas et al. | 424/426 |
| 5,371,191 A | 12/1994 | Poser et al. | 530/350 |
| 5,459,047 A | 10/1995 | Wozney et al. | 435/69.1 |
| 5,470,831 A | 11/1995 | Whitman et al. | 514/16 |
| 5,543,392 A | 8/1996 | Tomita et al. | 514/8 |
| 5,543,394 A | 8/1996 | Wozney et al. | 514/12 |
| 5,595,722 A | 1/1997 | Grainger et al. | 424/9.2 |
| 5,616,490 A | 4/1997 | Sullivan et al. | 435/366 |
| 5,631,142 A | 5/1997 | Wang et al. | 435/69.1 |
| 5,635,372 A | 6/1997 | Celeste et al. | 435/69.1 |
| 5,637,480 A | 6/1997 | Celeste et al. | 435/69.4 |
| 5,656,587 A | 8/1997 | Sporn et al. | 514/2 |
| 5,661,007 A | 8/1997 | Wozney et al. | 435/69.4 |
| 5,677,276 A | 10/1997 | Dickerson et al. | 514/8 |
| 5,703,043 A | 12/1997 | Celeste et al. | 514/12 |
| 5,705,477 A | 1/1998 | Sporn et al. | 514/2 |
| 5,846,770 A | 12/1998 | LaVallie et al. | 435/69.1 |
| 5,849,880 A | 12/1998 | Wozney et al. | 530/399 |
| 5,854,207 A | 12/1998 | Lee et al. | 514/2 |
| 5,866,364 A | 2/1999 | Israel et al. | 435/69.1 |
| 5,928,940 A | 7/1999 | Sampath et al. | 435/325 |
| 5,932,216 A | 8/1999 | Celeste et al. | 424/158.1 |
| 5,965,403 A | 10/1999 | Celeste et al. | 435/69.4 |
| 5,972,884 A | 10/1999 | Cohen et al. | 514/12 |
| 5,981,489 A | 11/1999 | Stevenson et al. | 514/15 |
| 5,994,094 A | 11/1999 | Hötten et al. | 435/69.1 |
| 6,051,648 A | 4/2000 | Rhee et al. | 525/54.1 |
| 6,120,760 A | 9/2000 | Hötten et al. | 424/85.1 |
| 6,124,273 A | 9/2000 | Drohan et al. | 514/55 |
| 6,150,328 A | 11/2000 | Wang et al. | 514/12 |
| 6,177,406 B1 | 1/2001 | Wang et al. | 514/12 |
| 6,197,550 B1 | 3/2001 | Hötten et al. | 435/69.5 |
| 6,211,157 B1 | 4/2001 | Benedict et al. | 514/21 |
| 6,468,960 B1 | 10/2002 | Lukanidin et al. | 514/2 |
| 6,498,142 B1 | 12/2002 | Sampath et al. | 514/12 |
| 6,992,066 B2 | 1/2006 | Akella et al. | 514/21 |
| 2002/0009789 A1 | 1/2002 | Hanyu et al. | 435/189 |
| 2002/0025340 A1 | 2/2002 | Dyer | 424/486 |
| 2002/0040004 A1 | 4/2002 | Benedict et al. | 514/21 |

(Continued)

FOREIGN PATENT DOCUMENTS

CN        1 163 780        11/1997

(Continued)

OTHER PUBLICATIONS

Chemical Abstract No. 132:40522x (Jan. 24, 2000).

(Continued)

*Primary Examiner*—Jeffrey Edwin Russel
(74) *Attorney, Agent, or Firm*—Williams, Morgan & Amerson, P.C.

(57) ABSTRACT

A liquid carrier medium is provided which is suitable for solubilizing growth factors, such as mixtures of bone morphogenetic proteins, that are found to induce an angiogenic response in ischemic tissues. The liquid medium comprises an aqueous solution of polyvinyl pyrrolidone.

13 Claims, 3 Drawing Sheets

U.S. PATENT DOCUMENTS

2003/0104977 A1    6/2003   Ripamonti et al. ............ 514/2

FOREIGN PATENT DOCUMENTS

| EP | 0 433 225 | 6/1991 |
|----|-----------|--------|
| EP | 0 516 901 | 12/1992 |
| EP | 0 747 066 | 12/1996 |
| WO | WO97/41880 | 11/1997 |
| WO | WO99/02674 | 1/1999 |
| WO | WO99/31136 | 6/1999 |
| WO | WO99/57146 | 11/1999 |
| WO | WO02/00244 | 1/2002 |
| WO | WO02/47713 | 6/2002 |

OTHER PUBLICATIONS

Mueller et al., *Swiss Medical Weekly* 131:23-25 (Jan. 12, 2001).
Procházka et al., *Journal of Reproduction of Fertility* 25:64, Abstract No. 173 (Jul. 2000).
Sakaguchi et al., *Theriogenology* 54:1327-1342 (2000).
Wiley et al., *Journal of Cellular Biochemistry* 19:383-394 (1982).
Laham et al., *J. Pharmacolo. Exp. Ther.* 292(2):795-802 (2000).
Yamamoto et al., *Basic Res. Cardiol.* 95(1):55-63 (2000).
Robinson et al., *Synthesis and Properties of PVP*, pp. 10-19, (date unknown).
Yonggang et al., *Journal of Xi'An Medical University* 22(2):132-133 (Apr. 2001) (English abstract only).
Cuevas et al., *Eur. J. Med. Res.* 4:403-410 (Oct. 15, 1999).
Folkman, *Circulation* 97:628-629 (1998).
Freed et al., *J. Biomed. Mater. Res.* 27:11-23 (1993).
Freedman et al., *J. Molecular and Cellular Cardiology* 33:379-393 (2001).
Hammerman, *Seminars in Nephrology* 15:291-299 (Jul. 1995).
Hirschberg et al., *Kidney International* 55:2423-2432 (1999).
Kawa-uchi et al., *Endrocrine* 3:833-837 (1995).
Nakaoka et al., *J. Clin. Invest.* 100:2824-2832 (Dec. 1997).
Nishida et al., *Spine* 23:2437-2442 (1998).
Parsons-Wingerter et al., *Microvasc. Res.* 55:201-214 (1998).
Ramoshebi et al., *Anta. Rec.* 259:97-107 (2000).
Schumacher et al., *Circulation* 97:645-650 (1998).
Stelnicki et al., *Plastic and Reconstructive Surgery* 101:12-19 (Jan. 1998).
Vukicevic et al., *J. Clin. Invest.* 102:202-214 (Jul. 1998).
Yamashita et al., *Exper. Cell Res.* 235:218-226 (1997).

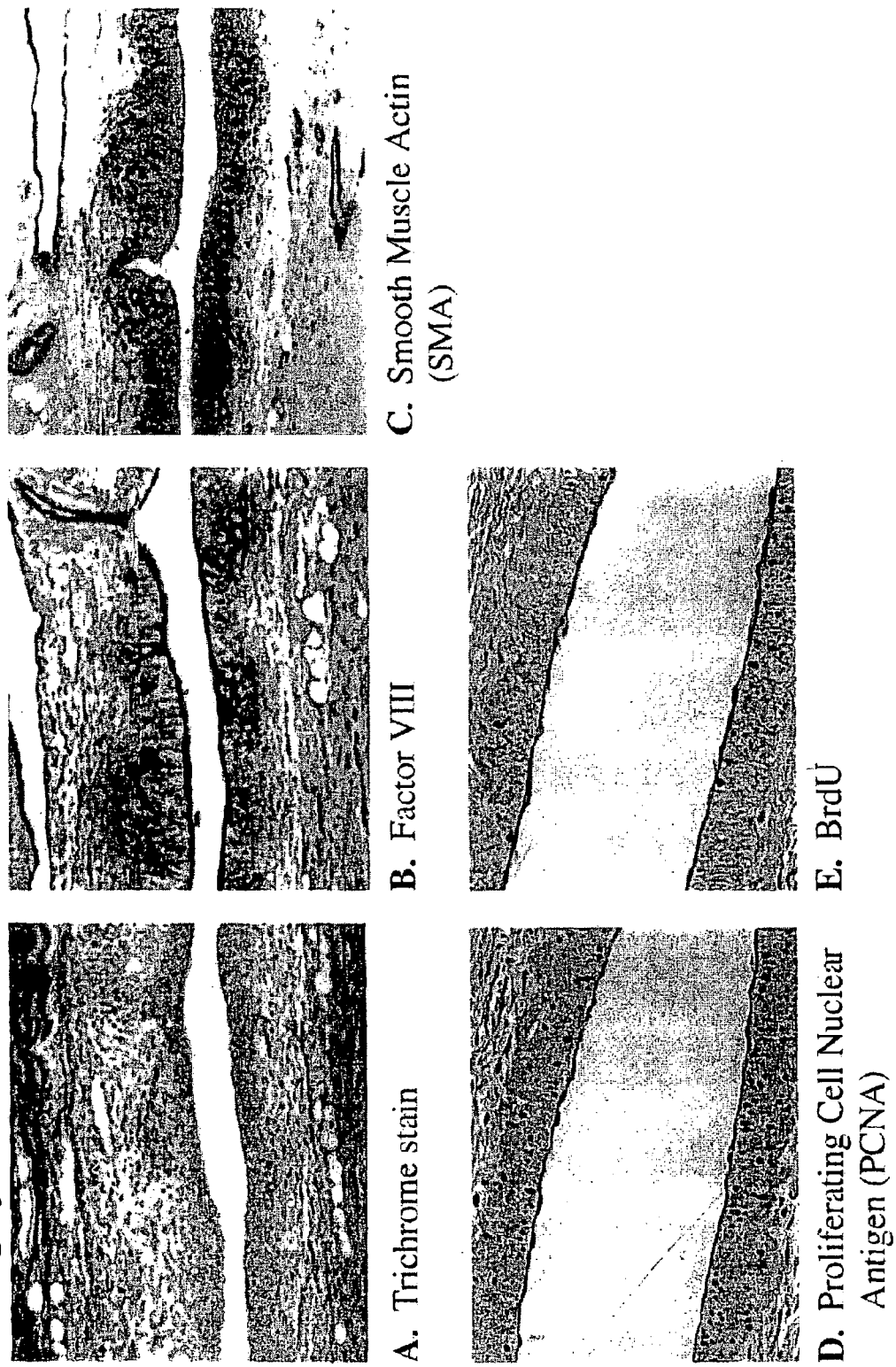
FIG. 1a-e: Histological sections of blood vessels formed in canine myocardium 2 weeks following injection of BDAP in 70% povidone
A. Trichrome stain
B. Factor VIII
C. Smooth Muscle Actin (SMA)
D. Proliferating Cell Nuclear Antigen (PCNA)
E. BrdU

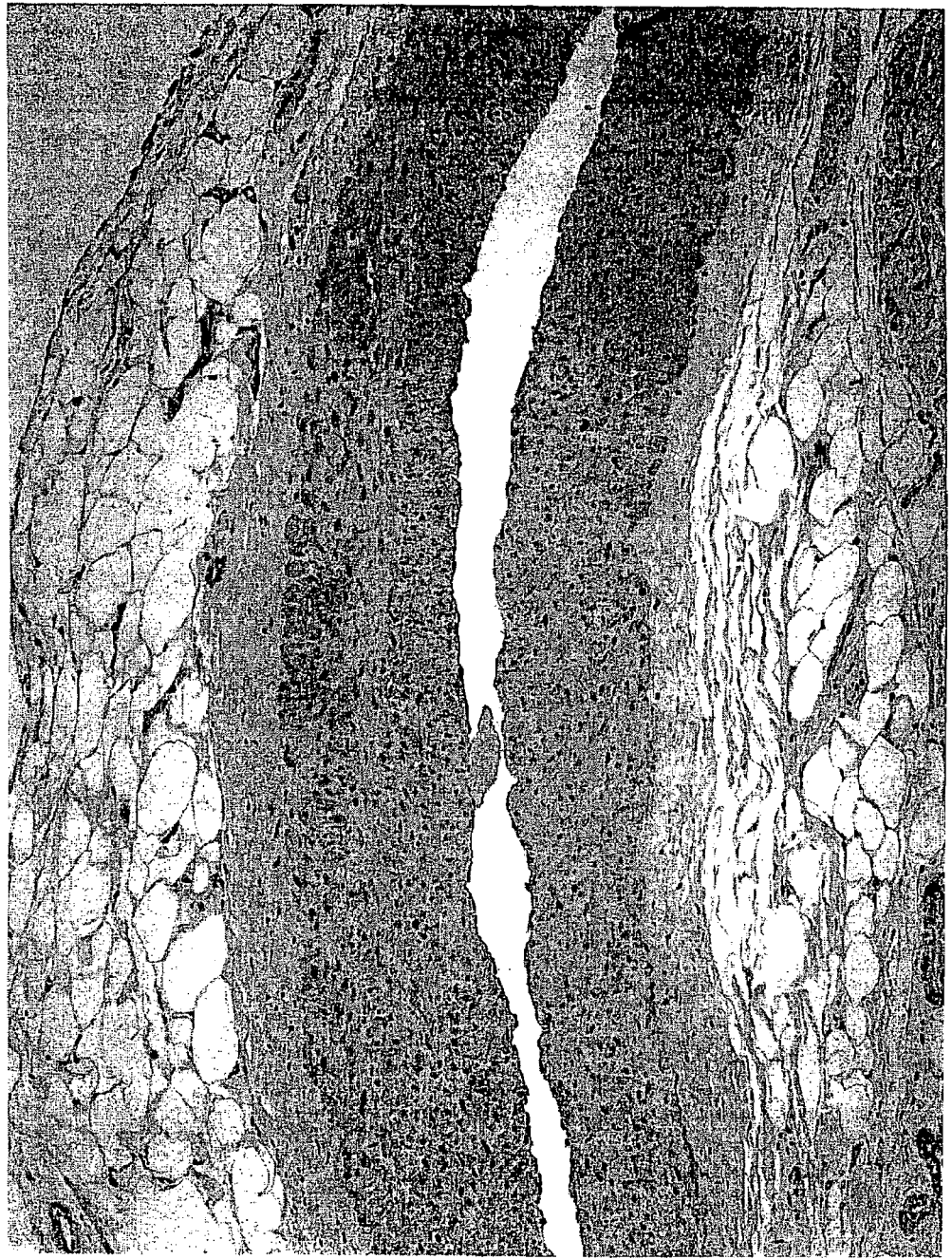
FIG. 2: 109-6-5M: Immunostaining of Smooth muscle cells and BRDU positive cells in sections of ischemic myocardium treated with GDF-5 solubilized in 1% povidone

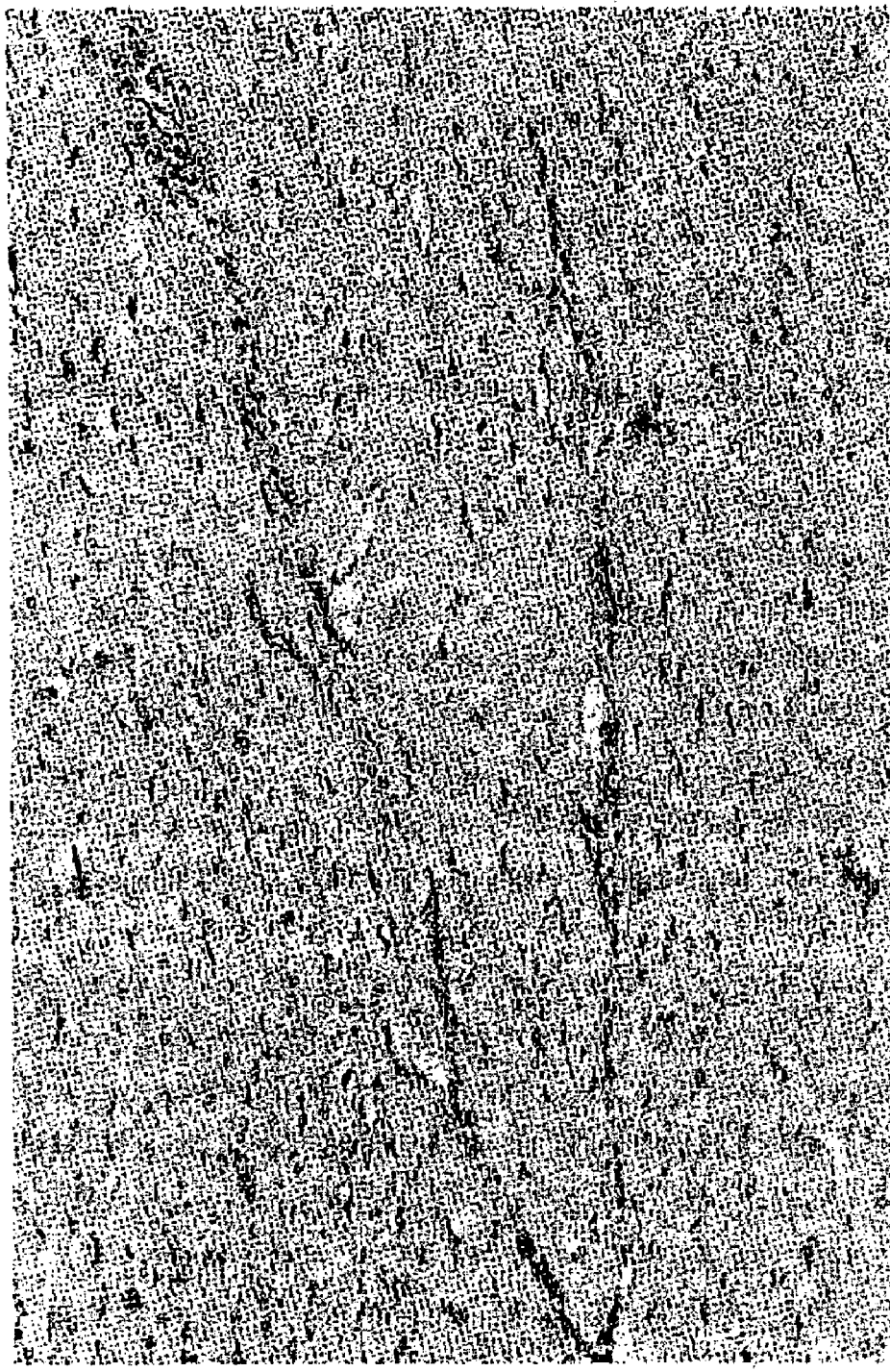
FIG. 3: TMR-GFM: Factor VIII immunostaining of a section of porcine myocardium that received GFm solubilized in 5% povidone.

POVIDONE-CONTAINING CARRIERS FOR POLYPEPTIDE GROWTH FACTORS

CROSS-REFERENCE TO RELATED APPLICATIONS

This application is a divisional of U.S. Ser. No. 10/027,669, filed Dec. 21, 2001, now issued as U.S. Pat. No. 6,992,066, which is a continuation-in-part of U.S. Ser. No. 09/748,038, filed Dec. 22, 2000 now U.S. Pat. No. 7,087,577 (which is incorporated herein by reference in its entirety), which is a continuation-in-part of U.S. Ser. No. 09/173,989, filed Oct. 16, 1998, now issued as U.S. Pat. No. 6,211,157 (Benedict et al.) and entitled "Protein Mixtures to Induce Therapeutic Angiogenesis" (which is also incorporated herein by reference in its entirety).

STATEMENT REGARDING FEDERALLY-SPONSORED RESEARCH OR DEVELOPMENT

Not applicable.

FIELD OF THE INVENTION

The present invention relates to the use of polyvinyl pyrrolidone (hereinafter "povidone") in a liquid medium for proteins and polypeptides, especially those which function as angiogenic growth factors.

BACKGROUND OF THE INVENTION

There are many medical circumstances in which an increase in the supply of blood to living tissue is indicated. These include: burns and wound healing, in which the incorporation of angiogenic factors into artificial skin may facilitate the formation of blood vessels in the healing wound bed and also reduce the risk of infection; cardiovascular disease, in which repair of anginal or ischemic cardiac tissue can be effected by the ingrowth of new blood vessels; stroke, where increased blood supply to the brain can reduce the risk of transient ischemic attack and/or cerebral arterial deficiency; and peripheral vascular disease, in which blood flow in the extremities is diminished. In each case, it is believed that the growth of new blood vessels will increase the volume of blood circulating through the tissue in question, and correspondingly increase the amount of oxygen and nutrients made available to that tissue.

One common cause of decreased blood flow is atherosclerosis. Atherosclerosis affects the blood vessels, including those of the heart, and is a major cause of cardiovascular disease, stroke and peripheral vascular disease. This disease may have its beginnings early in life and is initially characterized by a thickening of the arterial walls. This thickening typically comprises an accumulation of fat, fibrin, cellular debris and calcium. The resultant narrowing of the lumen of the afflicted vessel is called stenosis. Stenosis impedes and reduces blood flow. Hypertension and dysfunction of the organ or area of the body that suffers the reduced blood flow can result. As the buildup on the inner wall of a vessel thickens, the vessel wall loses the ability to expand and contract. Also, the vessel loses its viability and becomes weakened and susceptible to bulging, also known as aneurysm. In the presence of hypertension or elevated blood pressure, aneurysms will frequently dissect and ultimately rupture.

Small vessels, such as the arteries that supply blood to the heart, legs, intestines and other areas of the body, are particularly susceptible to atherosclerotic narrowing. When an artery in the leg or intestine is affected, the resultant loss of blood supply to the leg or segment of the intestine may result in gangrene. Atherosclerotic narrowing of one or more of the coronary arteries limits, and in some instances prevents altogether, blood flow to portions of the heart muscle. Depending upon the severity of the occlusion and its location within the coronary circulation system, pain, cardiac dysfunction or death may result. Because the consequences of blocked arteries are so serious, reliable treatments are highly desirable.

In many instances, it is possible to correct aneurysms and stenosis of major arteries using plastic reconstruction that does not require any synthetic graft or patch materials. In other instances, such as where the disease is extensive and the vessel is no longer competent, the blocked or weakened portion of the vessel is usually replaced with a graft. In such case, the affected vessel section is transected and removed and a synthetic patch, conduit or graft is sewn into its place. These types of procedures, including coronary artery bypass grafting (CABG) and percutaneous transluminal coronary angioplasty (PTCA), are routinely performed for the purpose of alleviating ischemia.

Nevertheless, coronary artery disease alone is responsible for approximately 550,000 deaths each year in the United States. Peripheral vascular disease results in lower limb amputation in about 150,000 patients each year, with a subsequent mortality rate of 40% within two years of amputation. Some of the difficulty in treating arterial occlusions may lie in the fact that each of the aforementioned surgical procedures is associated with a certain incidence of restenosis and may not be appropriate in certain instances. This is particularly true when the patient is elderly or has undergone a previous CABG or PTCA procedure. Accordingly, in such cases a less invasive technique would be preferred. In particular, it would be advantageous to be able to stimulate the surrounding tissue to produce for itself new vessels that would accommodate the volume of blood flow that has been occluded and thus compensate for the occluded vessels.

Angiogenic, or "vessel-growing" polypeptide growth factors in general have been the subject of much research. Such compositions offer the promise of a non-invasive, non-surgical treatment of arterial occlusion in a variety of situations, including those noted above. However, one major challenge facing the development of physiological treatments based on these materials is the lack of suitable solvents or carriers for the administration of growth factors to living patients.

A number of solvents have been used as carriers for particular applications within the pharmaceutical arts. Thus, for example, U.S. Pat. No. 5,981,489 (Stevenson et al.) discloses a number of non-aqueous protic formulations of peptides. Among the solvents mentioned therein are polyethylene glycols (PEGs), propylene glycol (PG), polyvinylpyrrolidone (PVP), methoxypropylene glycol (MPEG), glycerol, and glycofurol.

However, many solvents that adequately solubilize some pharmaceutical preparations and biological materials do not adequately solubilize polypeptide growth factors. Consequently, treatments utilizing such solvents may not induce an angiogenic response, even if the particular growth factor being used is capable of inducing such a response when properly delivered to the body of the patient. Other solvents tend to interact with, denature, induce crosslinking or cause other undesirable reactions in polypeptide growth factors, thus causing them to coagulate or precipitate, or otherwise rendering them pharmaceutically inactive or unsuitable. This is especially true if the solvent medium does not afford an acceptable pH range to the polypeptide growth factor (e.g., if it is too basic). Still other potentially useful solvents do not form stable solutions with growth factors, and hence cannot be used to make formulations having acceptable shelf stability.

Many potentially useful solvents for growth factors are also physiologically unsuitable. For example, investigators have used dilute solutions of hydrochloric acid (1 to 10 mM) to solubilize certain growth factors. See, e.g., R. J. Laham, M. Rezaee, M. Post, D. Novicki, F. W. Sallke, J. D. Pearlman, M. Simmons and D. Hung, "Intrapericardial Delivery of Fibroblast Growth Factor-2 Indices Neovascularization in a Procine Model of Chronic Myocardial Ischemia", J. Pharmocolo. Exp. Ther. 292(2), 795-802 (2000); N. Yamamoto, T. Kohmoto, W. Roethy, A. Gu, C. DeRosa, L. E. Rabbani, C. R. Smith, and D. Burkhoff, "Histological Evidence That Basic Fibroblast Growth Factor Enhances the Angiogenic Effects of Transmyocardial Laser Revascularization", J. Pharmocolo. Exp. Ther. 95(1), 55-63 (2000). However, for clinical applications, acid solvents such as dilute mineral acids are unsuitable because their use tends to cause cell damage or death in the proximity of the site of administration. On the other hand, saline solutions and neutral buffered salt solutions, which are more biologically compatible than mineral acids and which are used as solvents in some pharmaceutical formulations, cause many growth factor proteins to precipitate or become denatured, thus decreasing their bioavailability or effectiveness in the tissue.

The selection of a suitable solvent for growth factors is further complicated by other considerations. For example, even if a solvent adequately solubilizes a growth factor and does not cause it to become denatured or otherwise adversely affected, the solvent may nonetheless interfere with elution of the growth factor from the solvent medium, thereby reducing its efficacy. This may be the case, for example, if the solvent is too viscous, or bonds to the growth factor (e.g., through hydrogen bonding or dipole-dipole interactions) too strongly.

There is thus a need in the art for a solvent or carrier that solubilizes polypeptide growth factors sufficiently to render them pharmacologically useful, that does not cause them to coagulate, become denatured, or undergo crosslinking or other reactions that would adversely affect their pharmaceutical activity, that exhibits good shelf stability, that does not cause significant injury or damage to cells at the site of administration, and that allows the growth factor to properly elute from the solvent medium after administration to living tissues. These and other needs are addressed by the present invention, as hereinafter described.

BRIEF SUMMARY OF THE INVENTION

In one aspect, the present invention provides a composition comprising one or more polypeptide growth factors and a carrier medium therefor. The carrier is preferably an aqueous medium which solubilizes polypeptide growth factors sufficiently to render them pharmacologically useful, does not cause them to coagulate, become denatured, or undergo crosslinking or cause other reactions that would adversely affect their pharmaceutical activity. The present invention provides mixtures, solutions and compositions that exhibit good shelf stability, do not cause significant injury or damage to cells at the site of administration, and allow the growth factor to properly elute from the medium upon administration to living tissues.

The carrier medium comprises at least one compound, polymer or copolymer containing a lactam or pyrrolidone moiety, and preferably at least one compound, polymer or copolymer containing a vinyl lactam or vinyl pyrrolidone moiety. More preferably, the liquid medium comprises a solution of polyvinyl pyrrolidone, such as a polymer derived from N-vinyl-2-pyrrolidone, in an aqueous medium. Most preferably, the liquid medium comprises a water soluble homopolymer of N-vinyl-2-pyrrolidone, such as povidone, and water. Aqueous buffers which maintain the pH of the pyrrolidone moiety at or near the same pH as water may also be used, and the compositions may also include adjuvants and preservatives.

The carrier medium of the present invention may be combined with or used as a carrier or solvent for various growth factors, proteins, polypeptides and other such biological materials, including the various growth factors, matrix metalloproteinases, cytokines, and integrins that regulate angiogenesis. Thus, for example, the liquid media of the present invention may be used in conjunction with Vascular Endiothelial Growth Factor (VEGF), Transforming Growth Factor Beta (TGF-β), Fibroblast Growth Factors (FGF), Epidermal Growth Factors (EGF), angiogenin, TNF-alpha, insulin-like growth factor-1 (IGF-1), transforming growth factor α (TGF-α), platelet-derived growth factors (PDGF), Placental Growth Factors (PGF), Heparin-binding EGF-like Growth Factors (HEGF), Hepatocyte Growth Factors (HGF), Interferon-gamma (IFN-gamma), various Bone Morphogenic Proteins (BMP), growth/differentiation factors, vascular endothelial growth factors, and mixtures of any two or more of the foregoing materials.

BRIEF DESCRIPTION OF THE DRAWINGS

For a more detailed description of the present invention, reference will now be made to the accompanying Figures, wherein:

FIGS. 1A-E are histological sections of blood vessels formed in the canine myocardium following treatment with a protein mixture in accordance with the present invention; and FIGS. 2 and 3 are histological slides showing newly formed blood vessels in response to the treatment.

DETAILED DESCRIPTION OF THE PREFERRED EMBODIMENTS

Angiogenesis is a complex process involving several different cell types and molecular signaling events. Endothelial cells must secrete proteases to dissolve cell-cell and cell-matrix attachments, migrate and proliferate to form new vascular branches. Although single factors such as bFGF and VEGF have shown promise as angiogenic agents, it has been discovered that a more robust angiogenic response may be obtained through the use of an agent that comprises a mixture of proteins, a result which may be due in part to a synergistic effect of the combined proteins on the subject tissue.

Such protein mixtures preferably include the angiogenic mixtures of bone proteins described in commonly assigned U.S. Ser. No. 09/748,038, in U.S. Pat. No. 6,211,157 (Benedict et al.), in U.S. Pat. No. 5,290,763 and U.S. Pat. No. 5,371,191, all of which are incorporated by reference herein in their entirety. These mixtures may vary in composition and may be characterized in different ways. However, one way of characterizing the preferred compositions are as mixtures of proteins having residues comprising about 20-25 mole percent of acidic amino acids [ASP(+ASN) and GLU (+GLN)]; about 10-15 mole percent of hydroxy amino acids (SER and THR); about 35-45 mole percent aliphatic amino acids (ALA, GLY, PRO, MET, VAL, ILE, and LEU); about 4-10 mole percent aromatic amino acids (TYR and PHE); and about 10-20 mole percent basic amino acids (HIS, ARG and LYS). More preferably, the angiogenic protein mixture amino preferably has an amino acid composition of about 23.4 mole percent of acidic amino acids [ASP(+ASN) and GLU(+GLN)]; about 13.5 mole percent of hydroxy amino acids (SER and THR); about 40.0 mole percent aliphatic amino acids (ALA, GLY, PRO, MET, VAL, ILE, and LEU); about 6.8 mole percent aromatic amino acids (TYR and PHE); and about 16.6 mole percent basic amino acids (HIS, ARG and LYS) (TRP, CYS and ½ CYS were not measured and are not included in the calculation of mole percent).

Another way of characterizing the preferred protein mixtures are as mixtures containing at least two, and preferably all, of the following polypeptide growth factors: TGF-β1, TGF-β2, TGF-β3, BMP-2, BMP-3, BMP-4, BMP-5, BMP-6, BMP-7, and FGF-1. Preferred mixtures may also contain bone and/or serum proteins such as osteocalcin, osteonectin, albumin, transferrin, and APO-A1-LP, histones, RL-32, RS2D, and SPP24. These angiogenic growth factor mixtures may be employed to achieve a natural bypass effect by injecting the mixture into tissue in need of increased blood flow. Thus, for example, the mixtures may be used to induce vessel growth so as to heal a heart artery that has been blocked, or to promote angiogenesis in ischemic tissue so as to assist in recovery.

The bone-derived angiogenic protein (BDAP) mixtures preferred for use in the present invention are preferably administered to ischemic tissue in a suitable carrier or medium. These mixtures may be applied directly, e.g., through injection into the ischemic tissues, or indirectly, e.g., through intravenous administration. In some instances, it may be desired to apply the angiogenic factor in a carrier or medium that allows it to be absorbed quickly, while in other instances it may be desired to apply the angiogenic factor in a controlled, time-release manner. In still other instances, a single dose or other variation may be preferred. In general, the preferred carrier or medium will vary depending on the desired clinical application and/or site of administration.

Various materials may be combined with growth factors, proteins, polypeptides and other biochemical substances in mixtures and treatments made in accordance with the present invention. These materials may act to solubilize, stabilize, increase the bioavailability of, render pharmacologically useful, and/or facilitate the administration of such substances to a living subject. Such materials include, for example, polyactic acid, polyglycolic acid and its copolymers, collagen, PLURONIC® (polyoxyalkylene ether copolymer surfactant), vinylamide polymers and copolymers, vinylimide polymers and copolymers, and compounds, polymers and copolymers containing lactam or pyrrolidone moieties.

Typically, materials used in liquid media in accordance with the present invention will be materials that solubilize (or aid in the solubilization of) desired proteins, polypeptides, growth factors, or mixtures of the foregoing to a degree sufficient to render them pharmacologically useful and/or to increase their bioavailability. It is also preferred that materials employed as liquid media do not cause significant injury or damage to cells at the site of administration, and allow the material being solubilized to properly elute from solution upon administration to living tissues.

Liquid media comprising vinylamide polymers and copolymers, vinylimide polymers and copolymers, vinyl lactam monomers or copolymers, and compounds, polymers and copolymers containing lactam or pyrrolidone moieties may be used in various applications of the present invention. Preferably, however, the liquid media used in the present invention comprise at least one polymer derived from a vinyl pyrrolidone monomer or having a pyrrolidone moiety in its molecular structure. More preferably, these media comprise a polymer derived from N-vinyl-2-pyrrolidone. Most preferably, these media comprise a water soluble homopolymer of N-vinyl-2-pyrrolidone such as povidone.

The use of povidone (polyvinylpyrrolidone) in media compositions made in accordance with the present invention is especially preferred since it is commercially available in various pharmaceutical grades having various molecular weights, has good solubility in both aqueous and various organic media, and is found to solubilize a variety of proteins, polypeptides, growth factors, and mixtures of the foregoing sufficiently well to render them pharmacologically useful and/or to increase their bioavailability. Moreover, with proper choice of parameters such as viscosity, it is possible to formulate liquid media comprising povidone which allow the proper elution of growth factors from the media upon application of the same to living tissues. In some applications, parameters such as the viscosity of the liquid medium may be manipulated to advantageously control or achieve a desired rate of elution of active ingredients from the liquid medium.

Pharmaceutical grades of povidone suitable for use in the present invention are available commercially from International Specialty Products, Inc., Wayne, N.J., under the trademark Plasdone®. Properties of commercially available povidone are known in the art and may be obtained from a number of references, including "PVP: A Critical, Review of the Kinetics and Toxicology of Polyvinylpyrrolidone (Povidone)," Robinson, Sullivan, Borzelleca, and Schwartz, Lewis Publishers, Inc., 121 S. Main Street, P.O. Drawer 519, Chelsea, Mich., and "PVP polyvinylpyrrol idone Polymers", GAF(ISP) Technical Bulletin, 2302-203 SM-1290. Each of these grades may be employed in the liquid media of the present invention.

Povidone is available in a wide range of molecular weights and viscosities, reflecting polymers that consist of varying numbers of monomeric units. The different molecular weight grades of povidone are frequently characterized by their K-value, which is a measure of the mean molar mass of a polymeric substance and is derived from the relative viscosities of polymer solutions. The K-value of a polymer is related to its molecular weight by the Fikentscher equation (EQUATION 1), which provides that:

$$\log\frac{\eta_c}{\eta_0} = \left(\frac{75k^2}{1+1.5kc} + k\right)c \qquad \text{EQUATION 1}$$

where c is the concentration (in g/100 ml) of the polymer in solution, $\eta_c$ is the viscosity of the solution, $\eta_0$ is the viscosity of the solvent, and K=1000 k, wherein K is the K-value of the polymer. The Fikentscher equation is described in greater detail in H. Fikentscher, Cellusochemie, 1932, 13, 58-64 and 71-74.

K-values for a polymeric material can be obtained by dissolving the material in an appropriate amount of solvent so as to produce a dilute solution (e.g., about 1% by weight of the polymeric material, based on the total weight of the solution). The viscosity of the solution is then determined at 25° C., using, for example, a Höppler falling-ball viscometer or other means known in the art. The viscosity of the pure solvent is determined using the same viscometer. These values are then inserted into EQUATION 1, which is solved for k (and therefore K).

TABLE II describes the physical characteristics, including K-values, of some commonly available grades of povidone that may be used in the present invention:

TABLE II

Commercial Grades of Povidone

| Product | K-Value | Typical Molecular Weight[1] | Typical Viscosity[2] (cP) |
|---|---|---|---|
| Plasdone ® C-15 | 16-18 (16.1, 16.3) | 8,000 | 1.5 |
| Plasdone ® C-30 | 29-32 | 58,000 | 2.5 |
| Plasdone ® K-25 | 24-26 | 34,000 | 2.0 |
| Plasdone ® K-29/32 | 29-32 | 58,000 | 2.5 |
| Plasdone ® K-90/D | 85-95 (90) | 1,300,000 | 55.0 |

[1]Weight average, as determined by light scattering.
[2]5% solution in de-ionized water. Measured on a Brookfield LVT viscometer, 60 rpm @ 25° C.

The range of K-values noted in TABLE II reflects the product specifications set by the manufacturer (International Specialty Products, Inc., Wayne, N.J.), it being understood that the K-values of these products will vary from one product batch to another within the specified ranges. The parenthetical values are the actual K-values determined for particular product samples used in some of the experiments described herein, infra, as specified on the certificates of analysis that accompanied the samples. While povidone of varying K-values may be used in the practice of the present invention, the K-value of the povidone is preferably within the range of about 12 to about 100, more preferably within the range of about 15 to about 35, and most preferably within the range of about 16 to about 18.

Pyrrolidone-containing polymers useful in the present invention may have a variety of molecular structures. Thus, for example, they may be capped on one or more ends with at least one pyrrolidone moiety, they may have at least one pendant pyrrolidone moiety, or they may have a repeating unit or sequence comprising at least one pyrrolidone moiety. The polymer may also be a random, graft or block polymer or copolymer based on at least one vinyl pyrrolidone monomer, comonomer or copolymer. The polymers used in liquid media in the present invention which are derived from vinyl pyrrolidone may be grafted with lipophilic or hydrophilic radicals to make them more lipophilic or hydrophilic, respectively.

Various copolymers of vinyl pyrrolidone may also be employed in the practice of the present invention. These include, for example, copolymers formed from comonomers such as vinylacetate, ethyl acrylate, methyl acrylate, methyl methacrylate, dimethylaminoethyl methacrylate, acrylamide, methacrylamide, acrylonitrile, ethylene, styrene, maleic anhydride, acrylic acid, sodium vinylsulfonate, vinyl chloride, vinylpyridine, trimethyl (siloxy) vinylsilane, vinyl propionate, vinyl caprolactam, and methyl vinyl ketone. Such copolymers may be synthesized through polymerization in a solution, emulsion or suspension with a free radical initiator such as a peroxy or azo compound, through the use of transition metal catalysts, by photopolymerization techniques, or by other means as are known to the art.

Various monomers, polymers, and copolymers which are useful in the practice of the present invention or in the synthesis of materials useful in the present invention may be derived from vinyl pyrrolidone monomers in which the pyrrolidone ring and the vinyl functionality may be coupled to each other either directly or through various intermediate structures or moieties. Thus, for example, they may be joined by way of (a) a covalent bond; (b) an alkylene linkage, such as, for example, a methylene, ethylene, or propylene linkage; (c) an arylene linkage; (d) an alkylarylene linkage; (e) one or more hetero atoms, such as, for example, oxygen, nitrogen, or sulfur; (f) a functional group, such as, for example, a carboxyl, carbonyl, or amino linkage; or (h) a combination of any two or more of the foregoing. Preferably; the pyrrolidone ring and the vinyl functionality are joined together by way of a covalent bond between one of the vinyl carbon atoms and the nitrogen atom of the pyrrolidone ring. The vinyl moiety and pyrrolidone ring may also have various substituents. Such substituents may include, for example, alkyl groups such as, for example, methyl groups, or functional groups such as, for example, hydroxy groups. These substituents may also include deuterium for use in applications where it may be desirable to trace the progression or bioaccumulation, if any, of these materials in the body of a subject.

The vinyl pyrrolidone polymers and other polymeric materials useful in liquid media in accordance with the present invention may have various molecular weights. The properties of these polymers are found to vary with average molecular weight. Accordingly, the preferred range of average molecular weights will vary from one application to another, and will depend in part on the particular growth factor(s) or other treatments, substances or materials which need to be solubilized. However, in most applications, the average molecular weight will be from about 1 kD to about 130 kD and the material will comprise between 12 and 1350 monomeric units. Preferably, the molecular weight will be from about 1 kD to about 100 kD, more preferably from about 2.5 kD to about 90 kD, and most preferably from about 2.5 kD to about 20 kD. Compositions having a molecular weight of less than about 20 kD are especially preferred because they are readily cleared from the body, while some higher molecular weight compositions. (especially in the case of povidone) are found to undergo bioaccumulation.

The viscosity of the liquid medium will typically be less than about 3 centipoise (cP), preferably less than about 2.5 cP, more preferably less than about 2.0 cP, and most preferably less than about 1.5 cP (measured at 60 rpm@ 25° C.), as viscosities within these ranges are typically found to facilitate proper elution of growth factors and other such materials from the solvent medium and into the tissues of a treated subject. Moreover, viscosities within these ranges allow application of growth factors to a living subject through intravenous routes and by other non-invasive procedures. However, it is to be understood that higher viscosities may be warranted or desirable in certain situations, as, for example, where it would be desirable to apply growth factors and other such materials as a topical gel.

The compositions made in accordance with the present invention will typically have a pH within the range of about 1 to about 6, preferably within the range of about 4 to about 6, and most preferably of about 4.5. In the preferred pH range, the liquid medium will adequately solubilize many of the generally acidic growth factors without denaturing them or significantly affecting their activity in vivo, and the pH of the composition will not be so low as to cause necrosis or damage to living tissues, especially at the site of administration.

When vinyl pyrrolidone polymers are used in compositions of the present invention, they may in some instances be used in conjunction with other polymers, materials, solvents, or cosolvents. Thus, for example, these polymers may be used to form blends, mixtures, complexes, suspensions or polymeric networks with other polymers or materials.

As previously noted, the vinyl pyrrolidone polymers and other materials described above as being useful in the present invention may be used in liquid media for various growth factors, proteins, polypeptides and other such biological materials. Such biological materials include, for example, the novel mixtures of growth factors as have been described herein, as well as the various growth factors, matrix metalloproteinases, cytokines, and integrins that regulate angiogenesis. The latter group includes Vascular Endiothelial Growth Factors (VEGF), Transforming Growth Factors (TGF-beta), Fibroblast Growth Factors (FGF), Epidermal Growth Factors (EGF), angiogenin, and TNF-alpha. Other growth factors with which these materials may be used include Placental Growth Factors (PGF), Heparin-binding EGF-like Growth Factors (HEGF), Growth Differentiation Factors (GDF), Hepatocyte Growth Factors (HGF), and Interferon-gamma (IFN-gamma).

The vinyl pyrrolidone polymers and other materials described above may also be used in accordance with the present invention in liquid media for various other biological materials, including various Bone Morphogenic Proteins-(BMP) such as BMP-1 and the TGF-beta superfamily of proteins, including BMP-2-alpha, BMP-2-beta, BMP-3, BMP-3b, BMP-4, BMP-5, BMP-6, BMP-7, BMP-8, BMP-8b, BMP-9, BMP-10, BMP-11, BMP-12, BMP-13, BMP-14, BMP-15, TGF-beta-1, TGF-beta-2, TGF-beta-3, TGF-beta-4, and TGF-beta-5; growth/differentiation factors such as GDF-1, GDF-3, GDF-5, GDF-6, GDF-7, GDF-8, GDF-9, GDF-9B, GDF-10, GDF-11, and GDF-15; vascular endothelial growth factors such as VEGF-121, VEGF;-165, VEGF-183, VEGF-189, and VEGF-206; mitogenic proteins such as MP-52 (also called GDF-5) and MP-121; and mixtures of any two or more of the foregoing materials. Many of these materials have been at least partially characterized in the art, and some instances the complete nucleotide, DNA and/or amino acid sequences of these materials has been derived. Thus, for example, information regarding the nucleotide, DNA and amino acid sequences of MP-52 and MP-121 can be found in U.S. Pat. No. 6,120,760 (Hötten et al.), U.S. Pat. No. 6,197,550 (Hötten et al.), and U.S. Pat. No. 5,994,094 (Hötten et al.).

When liquid media comprising the vinyl pyrrolidone polymers and other materials described above are used in conjunction with various growth factors, proteins, polypeptides and other such biological materials or mixtures of biological materials as described above, the vinyl pyrrolidone polymers and other such materials may be present in the media at various concentrations. Typically, however, the vinyl pyrrolidone polymers and other such materials will be provided in water or an aqueous buffer capable of maintaining the pH within desired ranges that completely solubilize the polypeptide growth factors. In addition, the vinyl pyrrolidone polymers are provided in the water or aqueous buffer at concentrations ranging from the minimum concentration required to properly solubilize the desired growth factor or other biological material so as to produce a pharmacologically effective solution, up to the maximum solubility of the vinyl pyrrolidone polymer or other such material in the liquid medium.

Persons of skill in the art will appreciate that the optimal concentration of the vinyl pyrrolidone polymers and other such materials may vary, and may depend on factors such as the condition of the subject to which the solution is to be administered, the physiological effect which is desired, the desired viscosity of the treatment solution, and regulatory restrictions. In most applications, however, the concentration of these vinyl pyrrolidone polymers and other such materials will be from about 0.1% weight/volume to about 70% weight/volume. Preferably, the concentration of these materials will be from about 0.1% weight/volume to about 50% weight/volume; more preferably, the concentration of these materials will be from about 0.1% weight/volume to about 25% weight/volume; even more preferably, the concentration of these materials will be from about 0.1% weight/volume to about 15% weight/volume; even more preferably, the concentration of these materials will be from about 0.5% weight/volume to about 2.5% weight/volume; most preferably, the concentration of these materials will be about 1.0%. In the following examples, unless stated otherwise, all concentrations of povidone are in g/ml. As used herein, % weight/volume refers to the number of grams of the designated material dissolved in sufficient liquid (usually water) to yield 100 ml of solution. Thus, a 1% aqueous povidone (polyvinylpyrrolidone) solution consists of 1 g of povidone dissolved in sufficient water (or aqueous buffer) to yield 100 ml of solution.

The concentration and average molecular weight of the vinyl pyrrolidone polymers and other such materials described herein will typically be chosen to provide a medium that is sufficiently acidic to solubilize the growth factors and other biochemical materials employed in the mixtures and treatments described herein, while not being so viscous as to hinder the effective administration of these materials by the desired route or to prevent sufficient elution of these materials from the media as required for effective treatment.

Preferably, the vinyl pyrrolidone polymers and other such materials described above for use in liquid media in accordance with the present invention will be present in these media as mixtures with water or an aqueous buffer capable of maintaining a desired (typically acidic) pH range. Hence, the maximum amount of the vinyl pyrrolidone polymer or other such material present in the liquid medium will frequently be dictated at least in part by the solubility of the materials in water. The liquid medium may also contain other materials, including, but not limited to, excipients, surfactants (including, for example, non-ionic surfactants such as Tween 20) preservatives (including, for example, antimicrobial agent such as methyl or propyl parabens or benzyl alcohols), and cosolvents.

The methods and compositions disclosed and claimed herein can be made and executed without undue experimentation in light of the present disclosure. While the compositions and methods of this invention have been described in terms of preferred embodiments, it will be apparent to those of skill in the art that variations may be applied to the method and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following examples are intended to be merely illustrative, and do not limit the scope of the claimed invention.

EXAMPLE 1

Canine Myocardial Angiogenesis Pilot Study

This example illustrates the efficacy of BDAP solubilized in a 70% aqueous povidone (K-90) solution in treating ischemic myocardial tissues.

Four adult mongrel dogs of either sex, weighing 21-26 kg, were anesthetized and a left thoracotomy performed through the fifth intercostal space. All visible epicardial collaterals connecting LAD artery diagonals to circumflex or right coronary arteries were ligated to minimize collateral flow to the LAD artery territory and an ameroid constrictor was placed on the proximal to the first diagonal branch. After completing the procedure, BDAP was applied to both the ischemic and non-ischemic left circumflex (LCX) coronary artery region in three different concentrations and using three different methods of application, for a total of nine injections in each region for each animal. Thus, 0, 10 or 100 μg BDAP was injected in 1) a 0.1 cc volume of 70% ISP Plasdone® povidone having a K value of about K-90, 2) encapsulated in polymer microspheres suspended in povidone, or 3) dissolved/suspended in collagen gel for a total of nine injections. The chest was closed and the animal was allowed to recover.

In order to provide an index of cellular proliferation at multiple time points after the initial surgery, bromodeoxyuridine (BrdU, 25 mg/kg, Sigma, St. Louis, Mo.) was administered subcutaneously on post-operative days 2, 4, 6, 8, 10, 12, 14 and 21. After two or six weeks, the dogs were euthanized and the hearts explanted and cut into samples. Samples were fixed and serial sections, 4-5 microns thick, were cut and stained with Masson's trichrome stain to evaluate the general morphology of the myocardium. Sister sections were stained using standard immunohistochemical techniques with antibodies against bromodeoxyuridine (BrdU), PC10 proliferating cell nuclear antigen (PCNA), alpha smooth muscle actin (SMA) and Factor VIII using standard techniques.

Initial histological data (FIGS. 1A-E) indicate that 10 or 100 micrograms of BDAP suspended in 0.1 cc 70% ISP Plasdoneo® K-90 povidone stimulated blood vessel formation within two weeks post injection. Whereas control sections showed no significant vessel formation and the needle track was visible, BDAP-treated sections had several newly formed blood vessels, as evidenced by Masson's trichrome staining (FIG. 1A). Immunohistochemical staining demonstrated that these vessels are lined with endothelial cells (dark stain FIG. 1B) and surrounded by a layer of smooth muscle cells (brown stain FIG. 1C). Furthermore, PCNA- and BrdU-stained sections (FIGS. 1D-E) indicated that these vascular endothelial and smooth muscle cells were actively proliferating. Thus, based on the qualitative results of the canine study, it was concluded that BDAP stimulates formation of new differentiated blood vessels approximately 50-100 μm in diameter in canine myocardium. The collagen carrier appeared to induce cartilage formation at the site of the injection. The high molecular weight povidone used in these studies appeared to be accumulating in the tissue at the site of the injection and was not metabolized at sacrifice.

EXAMPLE 2

Large Scale Canine Myocardial Ischemia Study

This example illustrates the efficacy of various concentrations of BDAP in a 1% aqueous C-15 povidone solution in treating ischemic myocardial tissues.

The purpose of this study was to determine the effects of intramyocardial injections of Suizer's Growth Factor mixture (GFM) (BDAP, also known as Proyasc™) in a canine model of chronic myocardial ischemia. Thirty-eight (38) dogs underwent ameroid constrictor placement on the proximal LAD and ligation of visible epicardial vessels collateralizing the LAD territory. Three weeks later, during a second surgery, animals had intramyocardial injections of a 1% povidone (ISP Plasdone® C-15) solution containing either placebo, BDAP at a concentration of 1 μg/ml, or BDAP at a concentration of 10 μg/ml. Each injection consisted of 0.15 ml of treatment solution, and injections were made at a spatial density of ~1/cm$^2$ over the LAD region. Group assignments were random and investigators were blinded to group assignment until after the analysis of all test results. Each animal tested survived for an additional 6 weeks. Assessments of regional blood flow (by colored microspheres), angiography and echocardiography (rest and stress) were performed prior to and after treatment. Histology and necropsy were performed after sacrifice.

Results of this prospective, blinded, multifaceted assessment of the effects of BDAP solubilized in a 1% C-15 povidone solution showed that the treatment solution has a significant effect on vascular growth assessed histologically and by angiographic criteria. There was no significant effect on blood flow during maximal vasodilatory stress, though technical limitations resulted in inclusion of only a small number of studies for the analysis of maximal blood flow. There was a slight reduction in regional wall motion score during maximum dobutamine stress in the high concentration group, though global resting function was not influenced by treatment.

EXAMPLE 3

Porcine Myocardial Ischemia Study

This example demonstrates the effectiveness of a solution of BDAP in 5% aqueous C-15 povidone at treating ischemic tissues using a porcine model.

Twelve pigs (mean body weight 73±4.6 kg) were included in the study. The animals were premedicated with ketaminol (10 mg/kg) and atropine (2 mg/kg) injected intramuscularly. A vascular access was established through a vein in the ear. The animals were anaesthetized with sodium thiopental (5 m/kg) through this venous line and were intubated, and anaesthesia was maintained by intravenous administration of thiopental as needed. The animals were ventilated with room air. A left lateral thorocotomy was performed through the fifth intercostal space. The pericardium was opened and reflected to form a cradle for suspending the heart. In all animals, five triads of laser channels were drilled at the mid-height of the left lateral wall. Within each triad, the channels were 1 cm apart. The external opening of each channel was marked with a non-resorbable stitch in order to identify them later for histology. The animals were allocated randomly to receive an injection of either of 100 micrograms of growth factor in 0.1 ml of 1% povidone (ISD Plasdone® C-15) within the triads, or of the same amount of the carrier alone. At the end of the operation, the thoracotomy was closed on a chest tube, which was removed after weaning the animal from the ventilator. After 1 month, the animals were sacrificed and the hearts rapidly excised for histology.

As shown in FIG. 3, immunostaining for Factor VIII in sections of the ischemic myocardium taken from the animals treated with TMR and BDAP in 5% C-15 povidone indicated an increase in the number of vascular endothelial cells compared to no treatment or treatment with TMR alone. Thus, BDAP in 5% C-15 Plasdone stimulated the formation of new blood vessels in the subject animals.

EXAMPLE 4

Canine Myocardial Ischemia Study

This example demonstrates the effectiveness of a solution of GDF-5 in 1% aqueous C-15 povidone at treating ischemic tissues.

The experiment of EXAMPLE 1 was repeated using a solution of GDF-5 solubilized in 1% povidone (ISD Plasdone® C-15) as the treating solution in each case. As in EXAMPLE 1, BrdU-stained sections of the smooth muscle cells and BrdU positive cells in sections of the ischemic myocardium taken from the animals indicated that these vascular endothelial and smooth muscle cells were actively proliferating, thus indicating that GDF-5 in 1% C-15 povidone stimulated the formation of new differentiated blood vessels in the subject (FIG. 2).

The above-noted experimental results are summarized in TABLE 3. As the results demonstrate, aqueous solutions of polyvinyl pyrrolidone of varying molecular weight and at various concentrations can be used to solubilize various growth factors at various dosage levels. The resulting solutions have been shown to induce an angiogenic response in porcine and canine subjects, and hence would be expected to induce a similar response in human subjects.

TABLE 3

| | | Experimental Summary | | | |
|---|---|---|---|---|---|
| EX-AMPLE | Growth Factor(s) | Growth Factor Concentration (mg/cc) | Povidone Concentration (% wt/vol) | Povidone Molecular Weight | Subject |
| 1 | BDAP | 0, 0.1, 1.0 | 70% | K-90 (≈1,300,000) | Canine |
| 2 | BDAP | 0, 1, 10 | 1% | C-15 (≈8,000) | Canine |
| 3 | TMR-BDAP | 1.0 | 5% | C-15 | Porcine |
| 4 | GDF-5 | 0, 0.5, 2.5, 5.0 | 1% | C-15 | Canine |

Although various embodiments of the present invention are specifically illustrated and described herein, it will be appreciated that modifications and variations of the invention are covered by the above teachings and are within the purview of the appended claims without departing from the spirit and intended scope of the invention. For example, while it is preferred that the vinyl pyrrolidone polymers and other such materials described herein be incorporated into a liquid medium, persons skilled in the art will appreciate that, in some instances, these materials could also be advantageously employed in other media, such as, for example, solids, gels, or liquid crystals. Furthermore, the, examples set forth herein should not be interpreted to limit the modifications and variations of the invention covered by the claims, but are merely illustrative of some such possible variations.

What is claimed is:

1. A method for treating ischemic tissue, comprising the step of administering to a patient in need thereof, a growth factor composition comprising:
   a polypeptide of the TGF-β superfamily, and
   a carrier comprising a vinyl pyrrolidone polymer having a molecular weight of from about 2.5 kD to about 20 kD, and a solvent selected from the group consisting of water and aqueous buffer solutions,
   wherein the weight ratio of the polypeptide to the vinyl pyrrolidone polymer is 1:2 or less and the composition is capable of promoting angiogenesis when administered to a living subject at a site in need of such angiogenesis.

2. The method of claim 1, wherein the patient is human.

3. The method claim 2, wherein administering comprises injecting the growth factor composition into the patient's body.

4. The method of claim 2, wherein administering comprises injecting the growth factor composition into the patient's heart.

5. The method of claim 2, wherein administering comprises subcutaneous administration.

6. The method of claim 2, wherein administering comprises intramuscular administration.

7. The method of claim 2, wherein administering comprises intravenous administration.

8. The method of claim 1, wherein the ischemic tissue comprises myocardial tissue.

9. The method of claim 1, wherein administering comprises injecting the growth factor composition into the ischemic tissue.

10. The method of claim 1, wherein the growth factor composition is a liquid having a viscosity of less than about 3 cP.

11. The method of claim 10, wherein the composition is a liquid having a viscosity of less than about 2.5 cP.

12. The method of claim 11, wherein the composition is a liquid having a viscosity of less than about 2 cP.

13. The method of claim 12, wherein the composition is a liquid having a viscosity of less than about 1.5 cP.

* * * * *